(12) United States Patent
McIntyre

(10) Patent No.: US 10,145,737 B1
(45) Date of Patent: Dec. 4, 2018

(54) LASER INDUCED BREAKDOWN SPECTROSCOPY (LIBS) PROBE FOR SIMPLIFIED LIGHT COLLECTION AND LASER OPERATION

(71) Applicant: Energy, United States Department of, Washington, DC (US)

(72) Inventor: Dustin McIntyre, Washington, PA (US)

(73) Assignee: U.S. Department of Energy, Washington, DC (US)

(*) Notice: Subject to any disclaimer, the term of this patent is extended or adjusted under 35 U.S.C. 154(b) by 0 days.

(21) Appl. No.: 15/794,345

(22) Filed: Oct. 26, 2017

(51) Int. Cl.
| | |
|---|---|
| G01J 5/02 | (2006.01) |
| G01J 3/02 | (2006.01) |
| G01J 3/10 | (2006.01) |
| G01J 3/443 | (2006.01) |
| G02B 27/14 | (2006.01) |
| G02B 1/11 | (2015.01) |
| H01S 3/16 | (2006.01) |
| H01S 3/0941 | (2006.01) |
| H01S 3/08 | (2006.01) |
| G01N 21/71 | (2006.01) |

(52) U.S. Cl.
CPC ............ *G01J 3/021* (2013.01); *G01J 3/0208* (2013.01); *G01J 3/0218* (2013.01); *G01J 3/108* (2013.01); *G01J 3/443* (2013.01); *G01N 21/718* (2013.01); *G02B 1/11* (2013.01); *G02B 27/141* (2013.01); *H01S 3/08059* (2013.01); *H01S 3/08072* (2013.01); *H01S 3/0941* (2013.01); *H01S 3/1611* (2013.01); *H01S 3/1623* (2013.01); *H01S 3/1643* (2013.01); *G01N 2201/0636* (2013.01); *G01N 2201/06113* (2013.01); *H01S 2301/02* (2013.01)

(58) Field of Classification Search
CPC ...... G01J 1/1626; G01J 1/0477; G01J 1/0411; G01J 1/4257; G01N 21/95
See application file for complete search history.

(56) References Cited

U.S. PATENT DOCUMENTS

2014/0111798 A1* 4/2014 Scaggs ................. G01J 1/4257
356/237.2

OTHER PUBLICATIONS

Ayyalasomayajula et al., "Application of laser-induced breakdown spectroscopy for total carbon quantification in soil samples," Mar. 2012, Applied Physics, vol. 51, No. 7, pp. B149-B154. (Year: 2012).*

Moulton et al., "Recent advances in solid state lasers and nonlinear optics for remote sensing," 2003, Proceedings of SPIE, vol. 4893, pp. 193-202 (Year: 2003).*

Wiens et al, "Joint analysis by laser-induced breakdown spectroscopy (LIBS) and Raman spectroscopy at stand-off distances," 2005, Spectrochimica Acta Part A, vol. 61 pp. 2324-2334. (Year: 2005).*

* cited by examiner

*Primary Examiner* — Kiho Kim
(74) *Attorney, Agent, or Firm* — Karen L. Blouin; Michael J. Dobbs; Brian J. Lally

(57) ABSTRACT

A Laser Induced Breakdown Spectroscopy (LIBS) probe using a dove prism for the laser media. The use of a dove prism allows for the removal of two mirrors over prior art schemes. The use of the dove prism allows for the light from the spark to be analyzed from the return path.

14 Claims, 5 Drawing Sheets

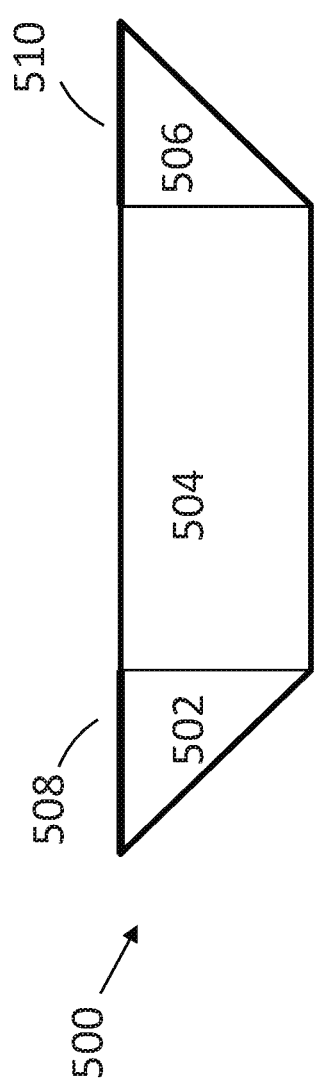

LASER INDUCED BREAKDOWN SPECTROSCOPY (LIBS) PROBE FOR SIMPLIFIED LIGHT COLLECTION AND LASER OPERATION

GOVERNMENT INTERESTS

The United States Government has rights in this invention pursuant to the employer/employee relationship between the inventors and the U.S. Department of Energy (DOE), operators of the National Energy Technology Laboratory (NETL) under Contract No.: DE-FE0004000.

FIELD OF THE INVENTION

The present invention relates to the use of a dove prism shaped laser source in Laser Induced Breakdown Spectroscopy (LIBS).

BACKGROUND OF THE INVENTION

Laser Induced Breakdown Spectroscopy (LIBS) is a powerful tool for qualitative and quantitative elemental, molecular and even isotopic analysis of materials. LIBS uses pulsed, solid state, lasers such as those made from Neodymium doped Yttrium Aluminum Garnet to generate short, powerful pulses that initiate dielectric breakdown on solids, in liquids and gases. This dielectric breakdown produces a bright flash of light at wavelengths that are characteristic of the elements present in the target. When the light is analyzed by a spectrometer, the identities of the elements present can be estimated and can be quantified when a gated spectrometer is used.

In LIES, the analysis operates by focusing the laser onto a small area at the surface of the specimen or into the specimen (gas/liquids), when the laser is discharged it ablates a very small amount of material, in the range of nanograms to picograms, which generates a plasma plume with temperatures typically in excess of 10,000 K. The local electric field density within the focal volume ionizes the molecules and element within it creating a large thermosluminescent emission initially. The relations or cooling of the hot gas allows for electron recombination. It is this process that releases the characteristic energy. During data collection, preferably after local thermodynamic equilibrium is established, plasma temperatures range from 5,000-20,000 K. At the high temperatures during the early plasma, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed and the characteristic radiation evaluated.

Prior art LIBS probe systems require an aligned intracavity Q-switch to generate the high peak power laserpulses. The Q-switching may be performed by an electro-optical or acoustic-optical element or a solid state saturable absorber known as a passive Q-switch. However the use of a Q-switch requires that the housing of the LIBS probe come equipped with at least four mirrors. The mirrors allow the LIBS light to bypass the laser rod and couple back into the fiber optic cable pumping the laser. Two of the four mirrors need to be dichroic mirrors produced through an extensive chemical vapor deposition process.

Therefore, a need persists in the industry for a LIBS system that avoids the need for four mirrors and attendant alignment, thereby reducing the complexity and the cost of the laser head.

SUMMARY OF THE INVENTION

According to one aspect of the invention, a laser induced breakdown spectroscopy (LIBS) probe has an optical fiber through which a pump beam is transmitted. A coupler is optically connected to the optical fiber. A first lens, having a shape and a coating, is optically connected to the coupler. The first lens collimates the pump beam. A first mirror, having a coating, is optically connected to the first lens. The first mirror reflects a predetermined wavelength of the pump beam. A second lens, having a shape and a coating, is optically connected to the first mirror. The second lens optically transmits the pump beam to a laser.

The laser has the shape of a dove prism with a first side. The first side has both a first and second coating. At least a portion of the first coating is optically connected to the second lens. The dove prism transmits an output pulse through the second coating. A second mirror, having a coating, is optically connected to the second prism coating. The second mirror reflects a predetermined wavelength of the output pulse. A third lens, having a shape and coating, is optically connected to the second mirror. The third lens focuses the output pulse such that it creates a spark.

According to another aspect of the invention, a return beam is transmitted from the third lens through the second and first mirrors to the coupler.

BRIEF DESCRIPTION OF THE DRAWINGS

Further aspects of the invention and their advantages can be discerned in the following detailed description, in which like characters denote like parts and in which.

DETAILED DESCRIPTION OF THE INVENTION

The present invention provides a Laser Induced Breakdown Spectroscopy (LIBS) probe. In the embodiment shown in FIG. 1, an optical fiber 102 connects to a coupler 104. In the illustrated embodiment, the coupler 104 is a mechanical coupler. In alternate embodiments, the coupler 104 may be a free space to fiber coupler or an optical coupler. In yet further embodiments the coupler 104 may be any type of coupler that yields acceptable results.

Figure 1:
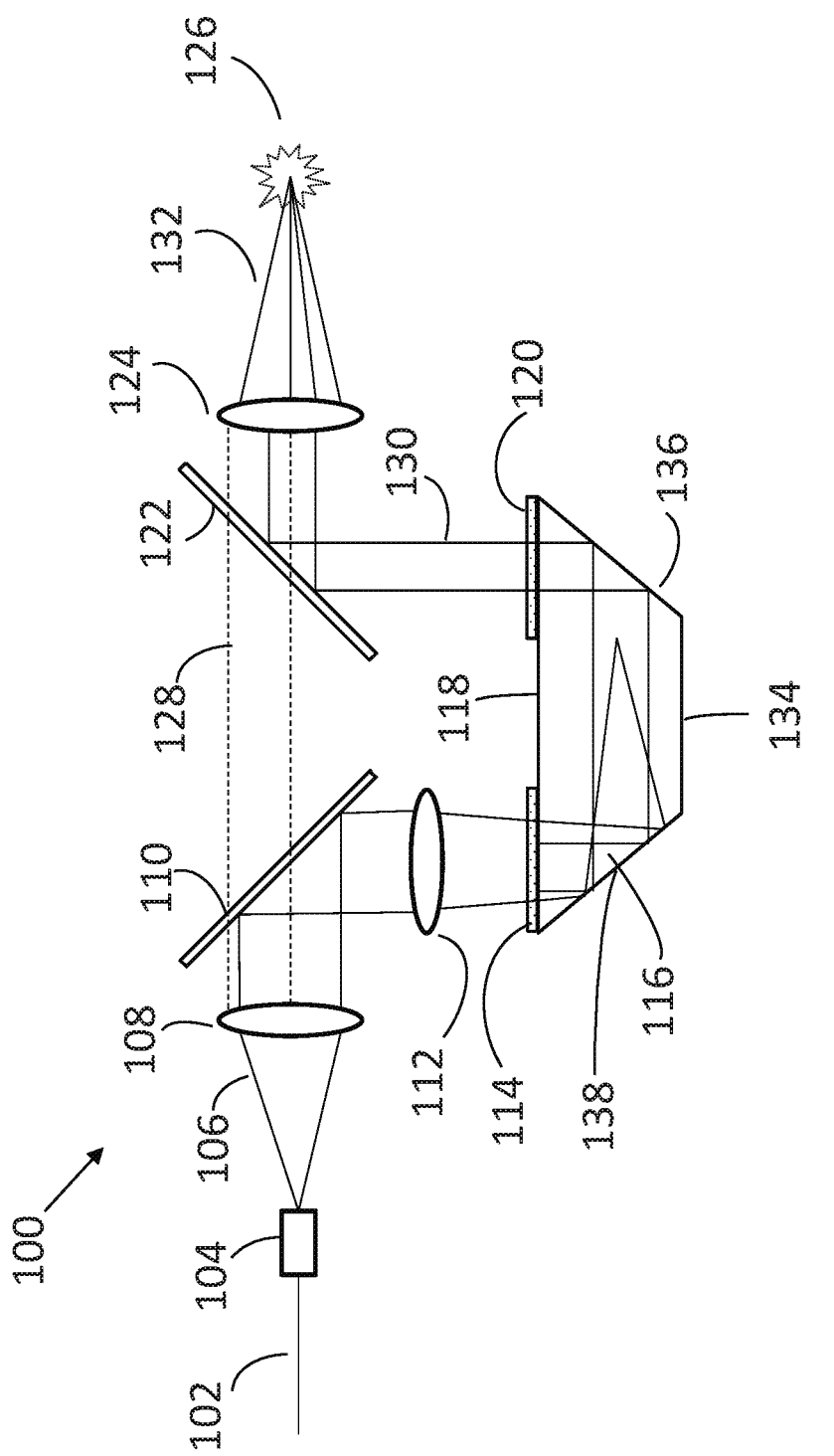
FIG. 1 is a schematic of the LIBS probe according to one embodiment of the invention.

As shown in FIG. 1, the optical fiber 102 carries a pump energy from an optical pumping source. The optical pumping source creates an optical pumping excitation energy or pump beam having low peak power, preferably less than 1,000 peak Watts, more preferably about 100-1,000 Watts, depending on the material of the laser media. The optical pumping excitation energy may be a single pulse, a continuous stream, or a series of pulses. The optical pumping source may be a laser diode providing optical pumping excitation energy in the form of a single square wave pulse. In such instances the single square wave pulse has a low power, preferably less than 1,000 peak Watts and a time duration of tens to several hundred microseconds. In other embodiments, the optical pumping source may be one or more vertical-cavity surface-emitting lasers (VCSEL).

Coupler 104 optically connects pump beam 106 to a first lens 108. The term optically connect refers to any means of optically transferring or optically transmitting between either directly or through any number of intermediate components. As shown in FIG. 1, the first lens may be a bi-convex lens. In alternate embodiments the first lens 108 may have a different shape. The first lens 108 may have a focal length of 1 to 5 centimeters. Preferably the first lens 108 is fused silica, sapphire, undoped yttrium aluminum garnet (YAG) or some other material that is transparent to the pump beam 106, has an appropriate index of refraction and a high optical damage threshold. The first lens 108 may be coated with an antireflection coating.

A first mirror 110 is optically connected to the first lens 108. The pump beam is optically transmitted to the first mirror 110 from the first lens 108. The first mirror 110 is a high reflectivity mirror. In a first embodiment the first mirror 110 comprises undoped yttrium aluminum garnet (YAG), fused silica, sapphire or a combination thereof, preferably further comprising one or more thin film optical coatings deposited onto one face. In a further embodiment, the first mirror 110 has a coating that is reflective to the pump beam 106 and partially reflective to the returning atomic emission 128. In one embodiment the coating is reflective to energy emitted at 808 nm.

In one embodiment, the first mirror 110 is coated with one of a plurality of coatings preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $Al_2O_3$. $Ta_2O_5$, $SiO_2$, $TiO_2$, $CaF_2$, $ZrO_2$, $BeO_2$, $MgF_2$, $LaF_3$ and $AlF_3$ or combinations thereof. The first mirror optically transmits the pump beam to a second lens 112.

A second lens 112 is optically connected to the first mirror 110. The second lens 112 may be a bi-convex lens. In alternate embodiments the second lens may have a different shape. The second lens 112 may have a focal point of 1 to 5 centimeters. Preferably the second lens 112 is fused silica, sapphire, undoped YAG or some other material that is transparent to the pump beam, has an appropriate index of refraction and a high optical damage threshold. The second lens 112 may be coated with an antireflection coating.

At least a portion of a laser media 116 is optically connected to the second lens 112. In the illustrated embodiment, the laser media 116 is in the shape of a trapezoidal dove prism. The laser media 116 or dove prism 116 has a first face 118 which is substantially flat. In one embodiment the first face 118 is substantially flat to a tolerance of λ/10 @632.8 nm. In further embodiments the first face 118 is substantially flat to a tolerance which produces acceptable results.

The dove prism 116 has a second face 134 opposed to the first face 118. The dove prism has a third face 136 and a fourth face 138 which each adjoin the first and second faces 118, 134. In the illustrated embodiment, the third and fourth faces 136, 138 are angled from the first face 118 at an angle of approximately 45 degrees. The 45 degree angled sides 136, 138 provide total internal reflection without the addition of external mirrors or coatings. Specifically, the angled sides 136, 138 causes the YAG material to act as a total internal reflector at both the pump wavelength (808 nm) and the laser output wavelength (1064 nm). Alternate embodiments may have third and fourth sides 136, 138 angled at different angles which may be greater than or less than 45 degrees such that a desired output pulse 130 is obtained.

Use of dove prism 116 allows for the removal of two mirrors over prior art schemes. The additional prior art mirrors are highly efficient throughout their reflection spectra but do introduce a small degree of loss of the light to be analyzed. By using a dove prism 116, the only mirrors that are in the system are coated for the narrow pump wavelength and the narrow laser output wavelength. The narrow bands do not interfere with the light from the spark 126. The light from the spark 126 that is useful for analysis is between 200-750 nm therefore the only losses that may occur though the return path are from the lenses 108, 124. Antireflective coating on the lenses 108, 124 minimizes the losses.

The shape of the dove prism 116 means that both the high reflector and output coupler of the cavity are already aligned and do not need any special attention during fabrication. The two angled sides of the trapezoidal shape provide total internal reflection without the addition of external mirrors or coatings. This allows the shape to be folded and thereby more compact.

The laser media 116 is formed from a material that emits an atomic optical emission when exposed to the pump beam 106 or pumping excitation energy 106. The laser media 116 is generally a host material that is doped. The host materials are preferably glasses, or crystals of oxides, garnets, vanadates, fluorides, or a combination thereof. The glasses are preferably doped with Nd, Er, or Yb. Oxides such as sapphire are preferably doped with Ti. The Garnets are preferably Yttrium Aluminum Garnet $Y_3Al_5O_{12}$ (YAG), Gadolinium Gallium Garnet $Gd_3Ga_5O_{12}$ (GGG), and Gadolinium Scandium Aluminum Garnet $Gd_3Sc_2Al_3O_{12}$ (GSGG) and are preferably doped with rare earths such as Nd, Tm, Er, Ho, Yb. The Vanadates or Yttrium Orthovanadate (YVO4) are preferably doped with Nd. The Fluorides or Yttrium Fluoride (YLiF4) are preferably doped with Nd. The laser media is preferably Nd:YAG (neodymium doped yttrium aluminum garnet), Nd:Glass (neodymium-doped glass), Nd:YLF (neodymium doped yttrium lithium fluoride), Nd:YVO4 (Yttrium Vanadate), Er:Glass (Erbium doped glass), Yb:YAG (ytterbium doped yttrium aluminum garnet), Alexandrite, Ti:Sapphire (Titanium sapphire), or a combination thereof. In the embodiment shown in FIG. 1, the laser media is formed from Co-Doped Nd/Cr:YAG which is grown as one crystal. In a further embodiment, the laser media is Nd:YAG having between about 0.5% and 3% atomic weight of Nd, which will emit an atomic optical emission at about 1064 nm. Alternate embodiments may have laser media 116 of different materials and varying proportions.

In operation, the pump beam 106 traverses the laser media 116 and interacts with and excites atoms, preferably Nd, within the laser media 116, inducing stimulated emission where the original photons from the emission energy cause the decay of an excited state. The stimulated event produces light of the same wavelength (about 1064 nm for a Nd:YAG laser media 116), phase, and in the same direction as the stimulating photon.

The dopant level of the laser media 116 is preferably low to improve performance. Lowering the dopant concentration affects the overall output by improving the beam overlap efficiency (side pumped), improving the pump light penetration depth (end pumped), improving the absorption depth of the optical pumping excitation energy, reducing thermal lensing losses, and reducing losses due to ASE (Amplified Spontaneous Emission). This leads to a more uniform pumped gain profile as well as more uniformly distributed thermal stresses which lessen the effects of thermal lensing. The reduction of dopant concentration lowers the gain of the material slightly but offers larger energy storage capacity in return. In one embodiment the dopant level of the Nd within the YAG crystal gain medium may be between 0.5 and 3.0% by weight. In a further embodiment the dopant level of the Nd within the YAG crystal gain medium may be 1.3% by weight. This allows the shape to be folded and thereby more compact.

Figure 2:
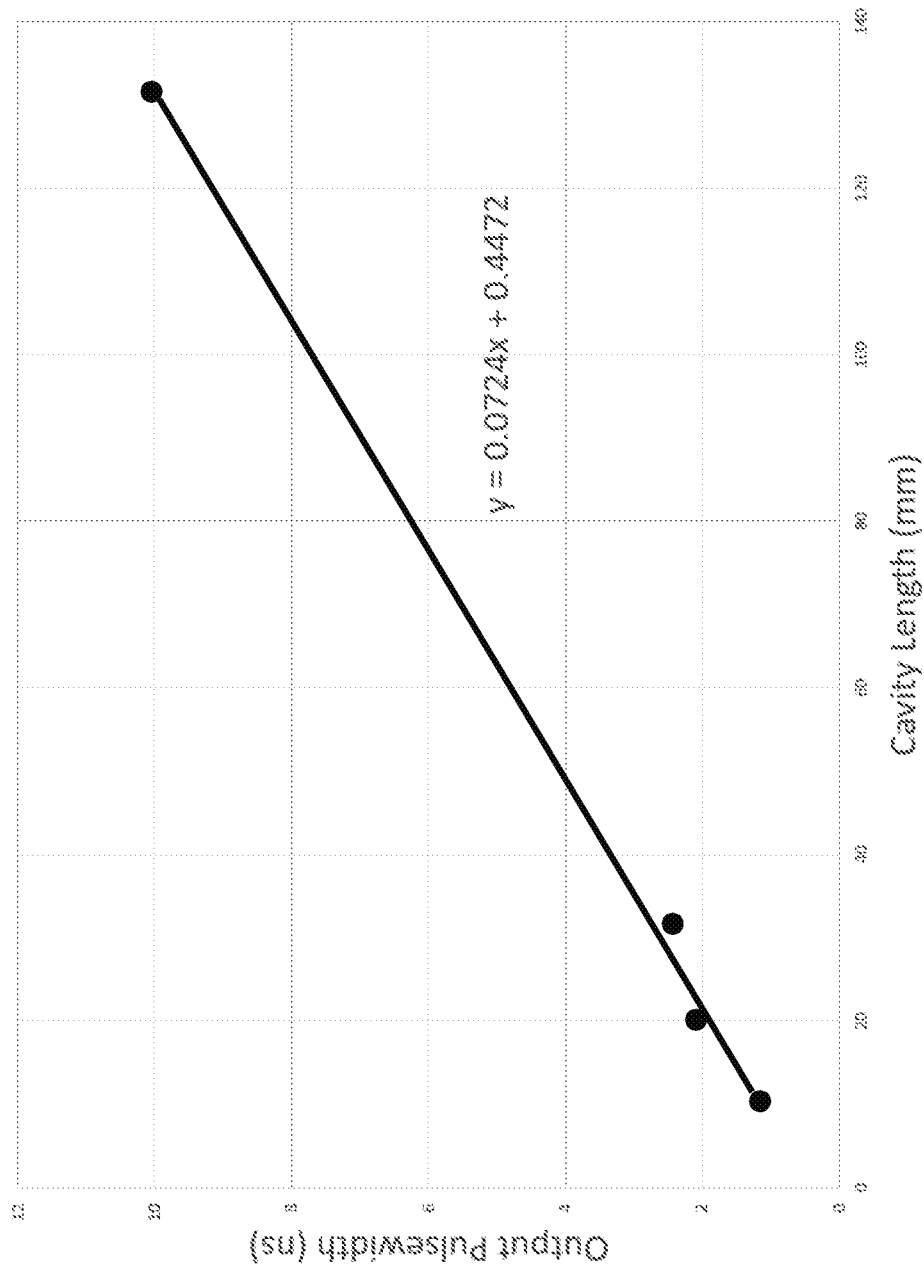
FIG. 2 is a graph demonstrating the relationship between cavity length and pulsewidth.

For a desired output pulse width the equation tr=2lc/c can be used. Where tr is the roundtrip time for a photon within the laser cavity, lc is the laser cavity length, and c is the speed of light in a vacuum. The linear relationship between cavity length and pulsewidth for passively Q-switched lasers is illustrated in FIG. 2. The laser media 116 can be optimized to provide a pulse width that is most appropriate for a particular application.

A portion of the first face 118 has a first coating 114 which is bonded directly to the laser media 116. In one embodiment the first coating 114 is a high reflector coating which is an antireflective coating to energy emitted at 808 nm and reflective to energy emitted at 1064 nm. In further embodiments the first coating 114 is one that produces acceptable results. At least a portion of the first coating 114 is optically connected to the second lens 112. The second lens 112 optically transmits the pump beam to the first coating 114 and laser media 116.

A portion of the first face 118 has a second coating 120 which is bonded directly to the laser media 116. In one embodiment the second coating 120 is high reflector coating which is partially reflective to energy emitted at 1064 nm and highly reflective to energy emitted at 808 nm. The second coating 120 comprises materials with various indices of refraction for example as $Al_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof. The second coating 120 is partially reflective to the atomic optical emission of the laser media. In one embodiment, the second coating 120 is deposited as an optical coating onto the face of the laser media 116 or bonded directly to the laser media 116. The length of the cavity dictates the output pulse width and can be tuned to provide a pulse width that is most appropriate for a particular application.

A second mirror 122 is optically connected to the second coating of the laser media 116 and the second mirror reflects the output pulse 130 which has a wavelength of 1064 nm. The coating on the second mirror 122 reflects the output pulse 130 and is partially reflective to the returning atomic emission. The second mirror 122 is a high reflectivity mirror. In a first embodiment the second mirror 122 comprises undoped yttrium aluminum garnet (YAG), fused silica, sapphire or a combination thereof, preferably further comprising one or more thin film optical coatings deposited onto one face. In a further embodiment, the second mirror 122 has a coating that is reflective to the output beam 106 and partially reflective to the returning atomic emission 128. In one embodiment the coating is reflective to energy emitted at 1064 nm.

In one embodiment, the second mirror 122 is coated with one of a plurality of coatings preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $Al_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof.

A third lens 124 is optically connected to the second mirror 122. As shown in FIG. 1, the third lens 124 may be a piano-convex lens. In alternate embodiments the third lens 124 may have a different shape. The third lens 124 focuses the output signal to a point 132 to create the spark 126. Light from the spark that is useful for analysis is between 200-750 nm. The third lens 124 focuses the output pulse. In the preferred embodiment, the third lens 124 is a piano-convex lens, preferably having a focal length of about 1-5 centimeters. Preferably, the third lens 124 is fused silica, sapphire, undoped YAG, or some other material that is transparent to the output pulse, has an appropriate index of refraction, and has a high optical damage threshold. In another embodiment the third lens 124 is a bi-convex lens. Preferably, the third lens 124 has an anti-reflection coating.

The third lens 124 also captures the light from the spark 126 and optically transmits the returning atomic emission 128 to the second mirror 122, the first mirror 110, the first lens 108 and finally the coupler 104. Preferably approximately 90% of the atomic emission is returned. The light from the spark 126 that is useful for analysis is between 200-750 nm.

In some embodiments the LIBS probe is used in an engine. If used in a laser spark plug design, information such as the air/fuel ratio during the ignition/combustion even can be determined and used as a measure of engine load and internal fuel/air mixing. The information can be used by the engine control computer to vary engine parameters to improve efficiency.

Figure 3:
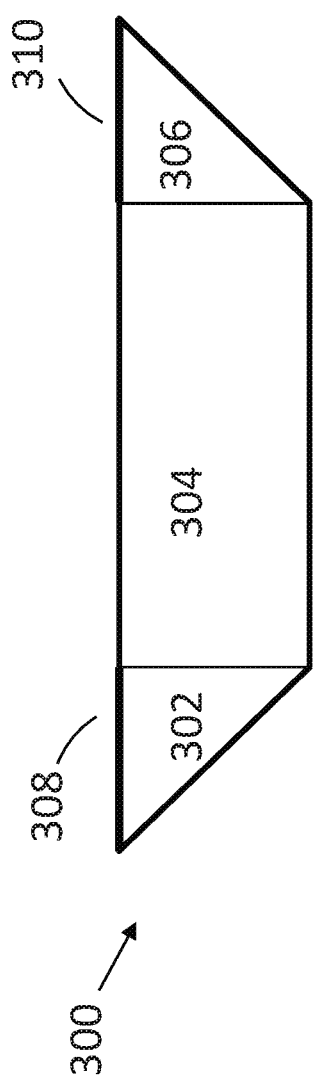
FIG. 3 is a plan view of a second embodiment of the laser media according to the invention.

In a second embodiment shown in FIG. 3, the laser media 300 is a substantially rectangular Co doped Nd (Cr: YAG) core 304 with two right angle prisms 302, 306 bonded to either end of the core 304 to complete the trapezoid 300. The prisms 302, 306 are made of undoped YAG or fused silica/quartz. A high reflector mirror 308 is bonded to right angle prism 302. An output coupler mirror 310 is bonded to right angle prism 306.

Figure 4:
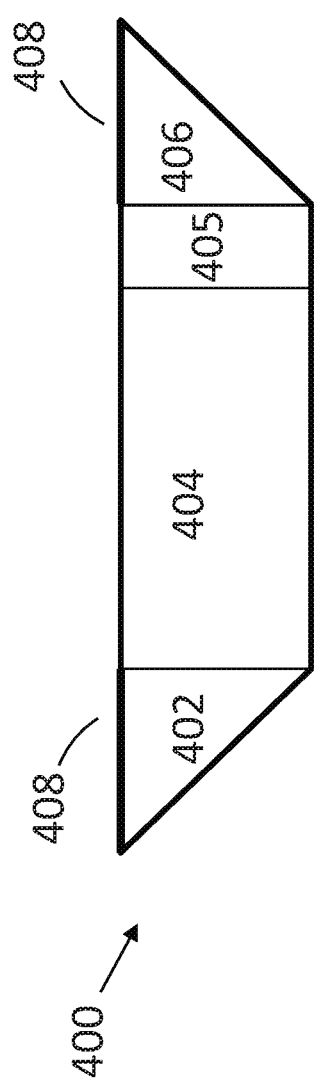
FIG. 4 is a plan view of a third embodiment of the laser media according to the invention; and, FIG. 5 is a plan view of a fourth embodiment of the laser media according to the invention.

In a further embodiment illustrated in FIG. 4, the laser media 400 is a substantially rectangular core formed from two different crystals, one Nd:YAG 404 for the gain media and the other doped with Cr for the switching media 405. Two right angle prisms (YAG) 402, 406 may be bonded to either end to of the core 404 to complete the trapezoid 400. A high reflector mirror 408 is bonded to right angle prism 402. An output coupler mirror 410 is bonded to right angle prism 406. In some embodiments the prisms 402, 406 may be cut out of the doped core 404, 405.

In yet another embodiment illustrated in FIG. 5, the laser media 500 is a substantially rectangular Nd:YAG core 504 with two right angle prisms 502, 506 bonded to either end of the core 504 to complete the trapezoid 500. One prism 402 is made of undoped YAG or Nd doped. The other prism 506 is made of Cr doped YAG. A high reflector mirror 508 is bonded to right angle prism 502. An output coupler mirror 510 is bonded to right angle prism 506.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C.§ 112, 6. In particular, the use of "step of" in the claims herein is not intended to invoke the provisions of 35 U.S.C.§ 112, 6.

The invention claimed is:

1. A laser induced breakdown spectroscopy (LIBS) probe, comprising:
    an optical fiber, a pump beam transmitted through the optical fiber;
    a coupler optically connected to the optical fiber;
    a first lens, the first lens optically connected to the coupler, the first lens having a predetermined shape and a first lens coating, the first lens collimating the pump beam;
    a first mirror, the first mirror optically connected to the first lens, the first mirror having a first mirror coating, the first mirror reflecting a predetermined wavelength of the pump beam;
    a second lens, the second lens optically connected to the first mirror, the second lens having a predetermined shape and a second lens coating, the second lens optically transmitting the pump beam to a laser;
    a laser, the laser having the shape of a dove prism, the dove prism having a first side, a first prism coating integrally formed with at least a portion of the first side, a second prism coating integrally formed with at least a portion of the first side and spaced from the first prism coating, at least a portion of the first prism coating optically connected to the second lens, the dove prism optically transmitting, through the second prism coating, an output pulse at a predetermined output pulse width;
    a second mirror, the second mirror optically connected to at least a portion of the second prism coating, the second mirror having a second coating, the second mirror reflecting a predetermined wavelength of the output pulse;
    a third lens, the third lens optically connected to the second mirror, the third lens having a predetermined shape and a third lens coating, the third lens focusing the output pulse such that it creates a spark.

2. The probe of claim 1, wherein a return beam is received at the coupler, the return beam being transmitted from the third lens through the second mirror, the second mirror optically transmitting a predetermined wavelength of the return beam and through to the first mirror, the first mirror optically transmitting a predetermined wavelength of the return beam to the first lens.

3. The probe of claim 1, wherein the pump beam has a wavelength of 808 nm.

4. The probe of claim 1, wherein the coupler is a free space to fiber coupler.

5. The probe of claim 1, wherein the first, second and third lenses have an antireflective coating.

6. The probe of claim 1, wherein the first mirror coating is highly reflective to light at a wavelength of 808 nm.

7. The probe of claim 1, wherein the second mirror coating is highly reflective to light at a wavelength of 1064 nm.

8. The probe of claim 1, wherein the dove prism has a second side opposed to and parallel to the first side, a third and a fourth side adjoining the first side at a 45 degree angle.

9. The probe of claim 1, wherein the length of the first side and the second side is such that there is total internal reflection of the pump beam inside the dove prism.

10. The probe of claim 1, wherein the dove prism is made from Neodymium doped Yttrium Aluminum Garnet.

11. The probe of claim 10, wherein the dopant level of Nd is between 0.5 and 3.0%.

12. The probe of claim 1, wherein the first prism coating is highly reflective to 1064 nm but partially reflective to 808 nm.

13. The probe of claim 1, wherein the second prism coating is partially reflective to 1064 nm but highly reflective to 808 nm.

14. The probe of claim 1, wherein the dove prism is formed from a substantially rectangular core having a first side and a second side opposed to the first side, a first right angle prism affixed to the first side and a second right angle prism affixed to the second side such that the dove prism has a trapezoidal shape.

* * * * *